US008715172B1

(12) United States Patent
Girgis

(10) Patent No.: US 8,715,172 B1
(45) Date of Patent: May 6, 2014

(54) DOUBLE BLADED LARYNGOSCOPE HAVING VIDEO CAMERA AND LIQUID CRYSTAL DISPLAY FOR FACILITATING INTUBATION PROCEDURE

(76) Inventor: Magdy S. Girgis, Monroe Township, NJ (US)

( * ) Notice: Subject to any disclaimer, the term of this patent is extended or adjusted under 35 U.S.C. 154(b) by 290 days.

(21) Appl. No.: 13/135,637

(22) Filed: Jul. 11, 2011

(51) Int. Cl.
*A61B 1/267* (2006.01)

(52) U.S. Cl.
USPC ........................................................ 600/188

(58) Field of Classification Search
USPC ......... 600/185, 188, 190, 193, 194, 196, 197,
600/198, 199, 201, 210, 213, 214, 216, 219,
600/221, 226, 239, 240
See application file for complete search history.

(56) References Cited

U.S. PATENT DOCUMENTS

| 5,827,178 | A | 10/1998 | Berall |
| 5,973,728 | A | 10/1999 | Levitan |
| 6,123,666 | A | 9/2000 | Wrenn et al. |
| 6,652,453 | B2 | 11/2003 | Smith et al. |
| 6,840,903 | B2 | 1/2005 | Mazzei et al. |
| 7,044,909 | B2 | 5/2006 | Berci et al. |
| 7,153,260 | B1 | 12/2006 | Girgis |
| 2001/0014768 | A1 | 8/2001 | Kaplan et al. |
| 2005/0192481 | A1 | 9/2005 | Berci et al. |
| 2006/0276693 | A1* | 12/2006 | Pacey ............................ 600/188 |
| 2007/0167686 | A1 | 7/2007 | McGrath |
| 2007/0179342 | A1 | 8/2007 | Miller et al. |
| 2008/0064926 | A1 | 3/2008 | Chen |
| 2009/0299146 | A1 | 12/2009 | McGrath |

* cited by examiner

*Primary Examiner* — Pedro Philogene
*Assistant Examiner* — David Comstock
(74) *Attorney, Agent, or Firm* — Richard L. Miller

(57) ABSTRACT

An improved double-bladed laryngoscope for recording and locally displaying an area of interest of a patient via a readily interchangeable and sterilizable visual image recorder and being of the type having a stationary handle, a stationary blade affixed to the stationary handle, a movable tip pivotally attached to the stationary blade, a movable tip arm pivotally attached to movable tip and movable handle, a movable blade pivotally attached to the stationary blade and affixed to movable handle by movable blade arm. When the movable tip at valleculla of a patient and the movable handle is moved towards the stationary handle will bend the movable tip lifting the epiglottis to uncover laryngeal opening (glottis). Simultaneously a movable blade pivotally attached to stationary blade and affixed to movable handle so as to allow movable blade to pivot away from stationary blade spreading posterior pharyngeal tissues and allowing space for intubating tube. A lock locks the movable blade in a desired positioned by locking the movable handle affixed thereto, and a camera arrangement for recording and locally displaying the area of interest of the patient. The improvement includes the camera arrangement running readily replaceably and interchangeably through the movable blade so as to be readily removable therefrom for sterilization without compromising the structural integrity of the movable blade.

24 Claims, 7 Drawing Sheets

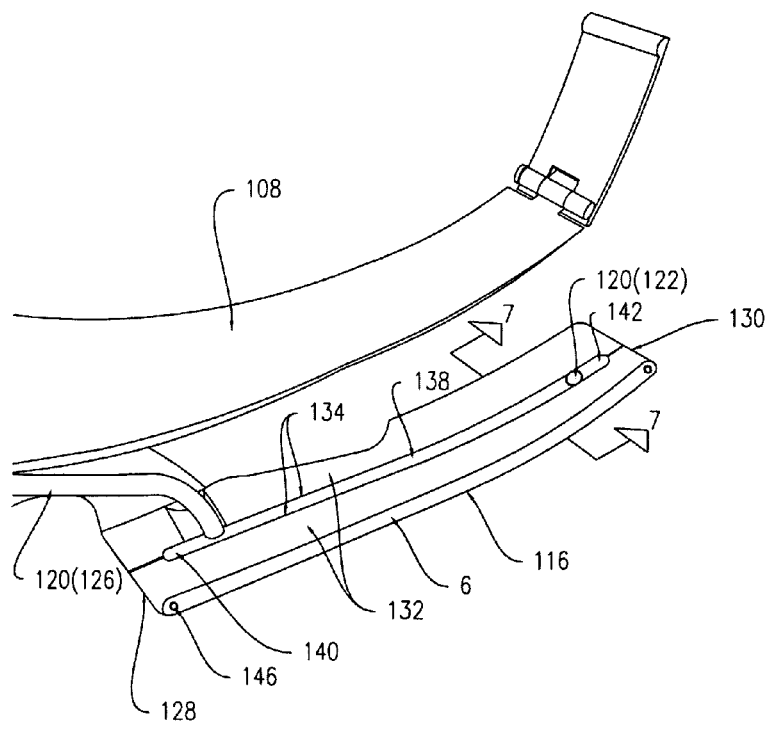
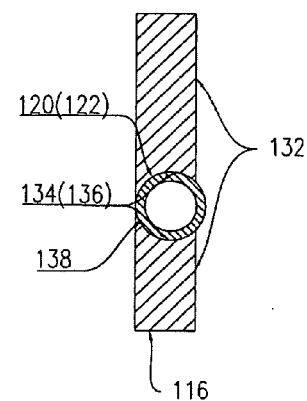
Fig 6
Fig 7

DOUBLE BLADED LARYNGOSCOPE HAVING VIDEO CAMERA AND LIQUID CRYSTAL DISPLAY FOR FACILITATING INTUBATION PROCEDURE

1. BACKGROUND OF THE INVENTION

A. Field of the Invention

The embodiments of the present invention relate to a double-bladed laryngoscope, and more particularly, the embodiments of the present invention relate to a double-bladed laryngoscope for recording and locally displaying an area of interest of a patient via a readily interchangeable and sterilizable visual image recorder and a blade therefor.

B. Description of the Prior Art

Numerous innovations for laryngoscopes have been provided in the prior art, which will be described below in chronological order to show advancement in the art, and which are incorporated herein by reference thereto. Even though these innovations may be suitable for the specific individual purposes to which they address, however, they differ from the present invention in that they do not teach a double-bladed laryngoscope for recording and locally displaying an area of interest of a patient via a readily interchangeable and sterilizable visual image recorder and a blade therefor.

(1) U.S. Pat. No. 5,827,178 to Berall.

U.S. Pat. No. 5,827,178 issued to Berall on Oct. 27, 1998 in U.S. class 600 and subclass 185 teaches a laryngoscope for use in intubating a patient's trachea, especially in emergency situations. The laryngoscope has a camera mounted in the vicinity of a distal end of its blade to observe the patient's trachea opening and other oral internal structures in a visual field. The camera is connected, typically via a fiberoptic cable, to a lightweight portable television screen, preferably, mounted on the laryngoscope handle, for displaying the visual field to a Professional Intubator so as to enable him or her to observe continuously the laryngeal opening and other oral internal structures as he or she manipulates the intubating instrument. The laryngoscope, with the camera and screen thereon, preferably, is held in one of the Professional Intubator's hands to lift and move aside the patient's tongue steadily and constantly. The other hand of the Professional Intubator then is free to manipulate the intubating instrument. Mounting the camera and the screen on the laryngoscope, which remains quite steady, provides the Professional Intubator with a continuous steady display of the laryngeal opening and other oral internal structures on the screen, while the intubator also sees directly down the patient's mouth.

(2) U.S. Pat. No. 5,973,728 to Levitan.

U.S. Pat. No. 5,973,728 issued to Levitan on Oct. 26, 1999 in U.S. class 348 and subclass 77 teaches a miniature video camera mounted on a pair of goggles, which substantially captures the monocular perspective of the operator's right eye during the medical procedure of direct laryngoscopy and tracheal intubation. The camera is connected to a pentaprism that the operator aligns with the area of interest by slight changes in head position and reference to alignment bands alongside the prism body. The image is reflected through the pentaprism to the camera and then displayed on a nearby video monitor. Auxiliary light sources or specialized equipment are not required. Persons other than the laryngoscopist can see the procedure as it is being performed.

(3) U.S. Pat. No. 6,123,666 to Wrenn et al.

U.S. Pat. No. 6,123,666 issued to Wrenn et al. on Sep. 26, 2000 in U.S. class 600 and subclass 188 teaches a laryngoscope equipped with a fiberoptic scope for enabling simultaneous remote observation of the airway and associated structures during insertion of the laryngoscope blade. The laryngoscope includes a blade member configured for attachment to a handle, and a conduit positioned adjacent the blade member for housing a fiberoptic scope. The fiberoptic scope includes fibers for illuminating an area adjacent a distal end of the blade, and viewing fibers for transmitting a visual image of the illuminated area to a remote viewing system. A clear cap is provided for the end of the conduit to protect the fiberoptic scope from patient secretions.

(4) United States Patent Application Publication Number 2001/0014768 to Kaplan et al.

United States Patent Application Publication Number 2001/0014768 published to Kaplan et al. on Aug. 16, 2001 in U.S. class 600 and subclass 188 teaches an intubating laryngoscope providing a standard handle, ready interchangeability of standard blades, a camera, and a magnifiable video display for easier and safer use in efficiently positioning an endotracheal tube through the vocal cords of a patient into the trachea, and for recordation in order to teach the procedure and for legal purposes.

(5) U.S. Pat. No. 6,652,453 to Smith et al.

U.S. Pat. No. 6,652,453 issued to Smith et al. on Nov. 25, 2003 in U.S. class 600 and subclass 188 teaches a laryngoscope for use in intubating a patient's trachea, in routine and emergency situations. The laryngoscope has a camera mounted in the vicinity of a distal end of its probe to observe the patient's laryngeal opening and transmit a signal to a display on the handle. The distal end of the probe also includes ovoid, generally C-shaped gripping apparatus, a pair of elongated grasping lips on the gripping apparatus, and an internal clamping assembly for controlling the gripping apparatus.

(6) U.S. Pat. No. 6,840,903 to Mazzei et al.

U.S. Pat. No. 6,840,903 issued to Mazzei et al. on Jan. 11, 2005 in U.S. class 600 and subclass 188 teaches a laryngoscope and viewing system configured to provide imaging of a patient's airway passage during intubation. In one embodiment, the device includes a handle, a blade attached to the handle, a flange attached to one side of the blade, a transmission cable connected to the opposite side of the blade, and a camera connected to the transmission cable. The camera is offset from the blade in at least one of the X plane and the Y plane.

(7) United States Patent Application Publication Number 2005/0192481 to Berci et al.

United States Patent Application Publication Number 2005/0192481 published to Berci et al. on Sep. 1, 2005 in U.S. class 600 and subclass 188 teaches a laryngoscope with a detachable camera. The system provides illuminating light to and images of the area ahead of the laryngoscope to facilitate insertion of the laryngoscope without damage to the surrounding tissue. The system includes a keyed attaching device for facilitating attachment of camera and laryngoscope in a correct orientation.

(8) U.S. Pat. No. 7,044,909 to Berci et al.

U.S. Pat. No. 7,044,909 issued to Berci et al. on May 16, 2006 in U.S. class 600 and subclass 185 teaches a combination laryngoscope and video display for providing images of the area ahead of the laryngoscope to facilitate insertion without damaging the surrounding tissue. The laryngoscope has a detachable blade and a rigid, detachable light and image guide attachment device for providing illuminating light ahead of the blade and for detecting the reflected light.

(9) U.S. Pat. No. 7,153,260 to Girgis.

U.S. Pat. No. 7,153,260 issued to Girgis on Dec. 26, 2006 in U.S. class 600 and subclass 196 teaches, as shown in FIG. 1, which is a diagrammatic perspective view of a typical prior art doubled bladed laryngoscope, a typical prior art laryngoscope 10 including a stationary handle 12, a stationary blade 14 affixed to the stationary handle 12, a movable tip 16 pivotally attached to a stationary blade 14, a movable handle 18 pivotally attached to the stationary blade 14, and a movable tip arm 20 pivoting the movable tip 16 and the movable handle 18. When the movable handle 18 is moved towards the stationary handle 12 will bend the movable tip 16 and will lift the epiglottis to uncover the laryngeal opening (glottis). Simultaneously the movable blade 22 pivotally attached to the stationary blade 14 and affixed to movable handle 18 as to allow movable blade 22 to pivot away from stationary blade 14 spreading the posterior pharyngeal tissues and allowing space for intubating tube. A lock 24 locks the movable blade 22 in a desired positioned by locking the movable handle 18 affixed thereto.

(10) United States Patent Application Publication Number 2007/0167686 to McGrath.

United States Patent Application Publication Number 2007/0167686 published to McGrath on Jul. 19, 2007 in U.S. class 600 and subclass 188 teaches medical devices for carrying out internal examination, such as laryngoscopes. The laryngoscope is provided with a camera element within a channel inside the blade.

(11) United States Patent Application Publication Number 2007/0179342 to Miller et al.

United States Patent Application Publication Number 2007/0179342 published to Miller et al. on Aug. 2, 2007 in U.S. class 600 and subclass 188 teaches a wireless laryngoscope having a first and a second handle portion coupled together defining an internal cavity and combining to form a handle assembly. The laryngoscope further includes a first and a second blade portion coupled together and defining an internal cavity in at least a portion thereof and combining to form a blade assembly. A light source within the internal cavity of the blade assembly illuminates at least a portion of the blade assembly. A camera mounted within the internal cavity of the blade assembly obtains images of the operation of the laryngoscope. A transmitter is coupled to the camera and is mounted within one internal cavity, with an antenna mounted within one internal cavity coupled to the transmitter. The transmitter wirelessly transmits the video images of the camera to a remote receiver.

(12) United States Patent Application Publication Number 2008/0064926 to Chen.

United States Patent Application Publication Number 2008/0064926 published to Chen on Mar. 13, 2008 in U.S. class 600 and subclass 110 teaches a laryngoscope for wireless image transmission, which has a handle and a blade. The handle has a power device and a terminal connecting to the power device. The blade is mounted detachably on the handle and has a camera with LED and a contact connecting to each other. A wireless transmitter connects to the camera with the LED to send the image. The blade is inserted into the mouth of the patient to lean against the patient's tongue. The throat can be lighted by the camera with the LED and the image can be transferred wirelessly to a screen.

(13) United States Patent Application Publication Number 2009/0299146 to McGrath.

United States Patent Application Publication Number 2009/0299146 published to McGrath on Dec. 3, 2009 in U.S. class 600 and subclass 188 teaches a laryngoscope blade that improves the transmission of light from the laryngoscope to enhance the amount of light reflected from an area of interest in a patient. The laryngoscope blade has a channel that extends at least partially though the blade and receives a light source. The channel has a substantially transparent end face that is situated towards the blade end and has an optical element adapted to reduce the ambient light signal from the light source in the channel.

It is apparent that numerous innovations for laryngoscopes have been provided in the prior art that are adapted to be used. Furthermore, even though these innovations may be suitable for the specific individual purposes to which they address, however, they would not be suitable for the purposes of the embodiments of the present invention as heretofore described, namely, a double-bladed laryngoscope for recording and locally displaying an area of interest of a patient via a readily interchangeable and sterilizable visual image recorder and a blade therefor.

2. SUMMARY OF THE INVENTION

Thus, an object of the embodiments of the present invention is to provide a double-bladed laryngoscope for recording and locally displaying an area of interest of a patient via a readily interchangeable and sterilizable visual image recorder and a blade therefor, which avoids the disadvantages of the prior art.

Briefly stated, another object of the embodiments of the present invention is to provide an improved double-bladed laryngoscope for recording and locally displaying an area of interest of a patient via a readily interchangeable and sterilizable visual image recorder and being of the type having a stationary handle, a stationary blade affixed to the stationary handle, a movable tip pivotally attached to the stationary blade, a movable tip arm pivotally attached to the movable tip and movable handle. When the movable tip at vallecula of a patient and a a moveable handle is moved towards the stationary handle will bend, the movable tip lifting the epiglottis to uncover laryngeal opening (glottis). Simultaneously a movable blade pivotally attached to the stationary blade and affixed to the movable handle by a movable blade arm so as to allow movable blade to pivot away from the stationary blade spreading posterior pharyngeal tissue and allowing space for intubating tube. A lock locks the movable blade in a desired positioned by locking the movable handle affixed thereto, and a camera arrangement for recording and locally displaying the area of interest of the patient. The improvement includes the camera arrangement running readily replaceable and interchangeably through the movable blade so as to be readily removable therefrom for sterilization without compromising the structural integrity of the movable blade.

The novel features considered characteristic of the embodiments of the present invention are set forth in the appended claims. The embodiments of the present invention themselves, however, both as to their construction and to their method of operation together with additional objects and advantages thereof will be best understood from the following description of the specific embodiments when read and understood in connection with the accompanying drawing.

3. BRIEF DESCRIPTION OF THE DRAWING

The figures of the drawing are briefly described as follows:

FIG. 6 is an enlarged diagrammatic perspective view of the movable blades identified by ARROW 6 in FIGS. 3-5;

FIG. 7 is an enlarged diagrammatic cross sectional view taken along LINE 7-7 in FIG. 6.

4. LIST OF REFERENCE NUMERALS UTILIZED IN THE FIGURES OF THE DRAWING

Figure 1:
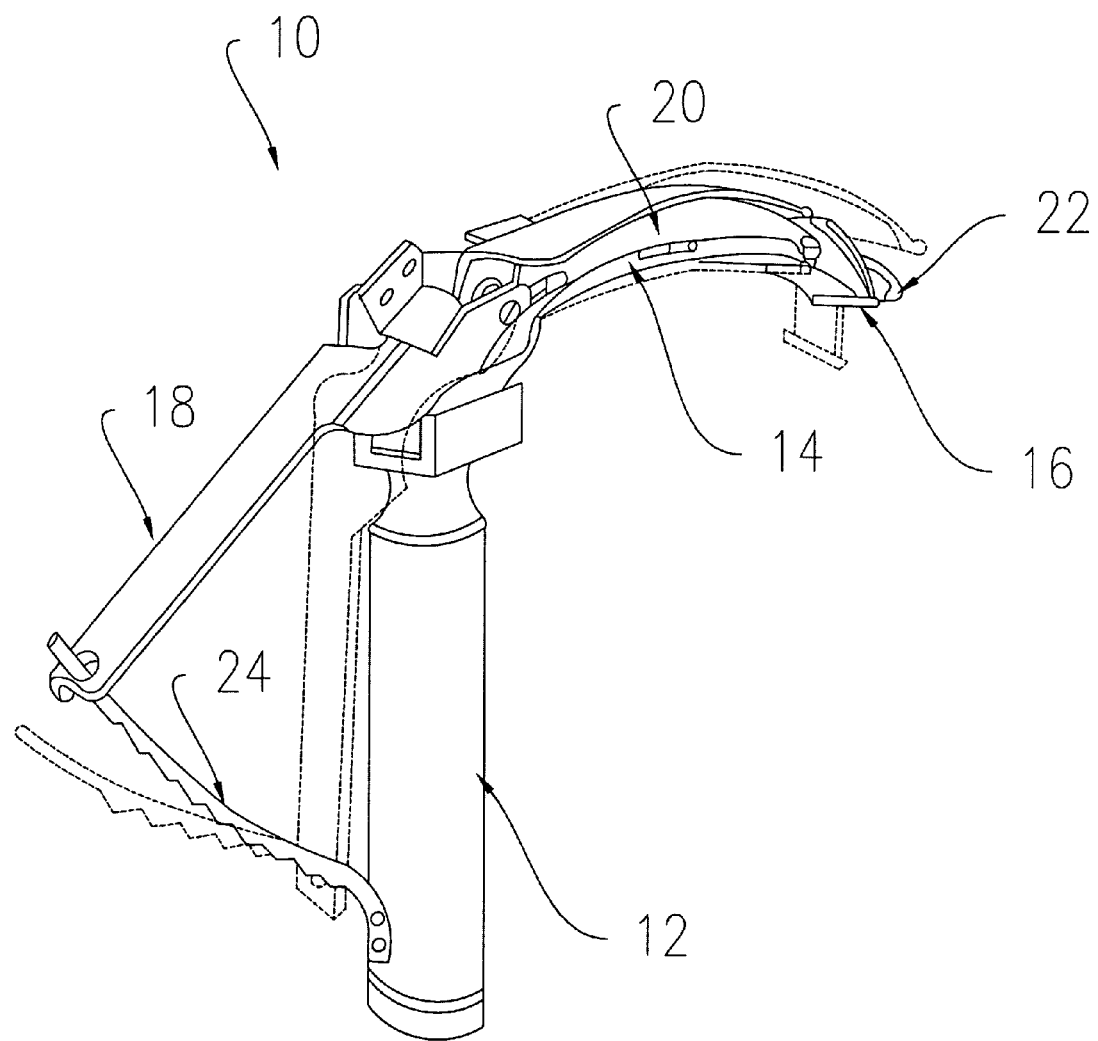
FIG. 1 is a diagrammatic perspective view of a typical prior art doubled bladed laryngoscope.

A. Prior Art.
10 typical prior art laryngoscope
12 stationary handle
14 stationary blade
16 movable tip
18 movable handle
20 movable tip arm
22 movable blade
24 lock
B. General.
100 double-bladed laryngoscope of embodiments of present invention for recording and locally displaying area of interest 102 of patient 103 via readily interchangeable and sterilizable visual image recorder 104
102 area of interest of patient 103
103 patient
104 visual image recorder
105 valleculla
C. Overall Configuration of Double-Bladed Laryngoscope 100.
106 stationary handle
108 stationary blade
110 movable tip
112 movable handle
114 movable blade arm
116 movable blade
118 lock
120 camera arrangement for recording and locally displaying area of interest 102 of patient 103
122 camera of camera arrangement 120
124 display of camera arrangement 120 for allowing viewing at display 124 of camera arrangement 120 area of interest 102 of patient 103 recorded by camera 122 of camera arrangement 120
126 conduit of camera arrangement 120
D. Specific Configuration of Movable Blade 116, Camera 122 of Camera Arrangement 120, and Conduit 126 of Camera Arrangement 120.
(1) Movable Blade 116.
128 proximal end of movable blade 116
130 free distal end of movable blade 116
132 two separate and distinct parts of movable blade 116
134 facing surfaces of two separate and distinct parts 132 of movable blade 116
136 complementary channel portions in facing surfaces 134 of two separate and distinct parts 132 of movable blade 116
(2) Camera 122 of Camera Arrangement 120.
138 shell of camera arrangement 120
140 proximal end of shell 138 of camera arrangement 120
142 distal end of shell 138 of camera arrangement 120
144 pair of through bores through each separate and distinct part of two separate and distinct parts 132 of movable blade 116
146 pair of screws of movable blade 116

5. DETAILED DESCRIPTION OF THE PREFERRED EMBODIMENTS

A. General.

Figure 2:
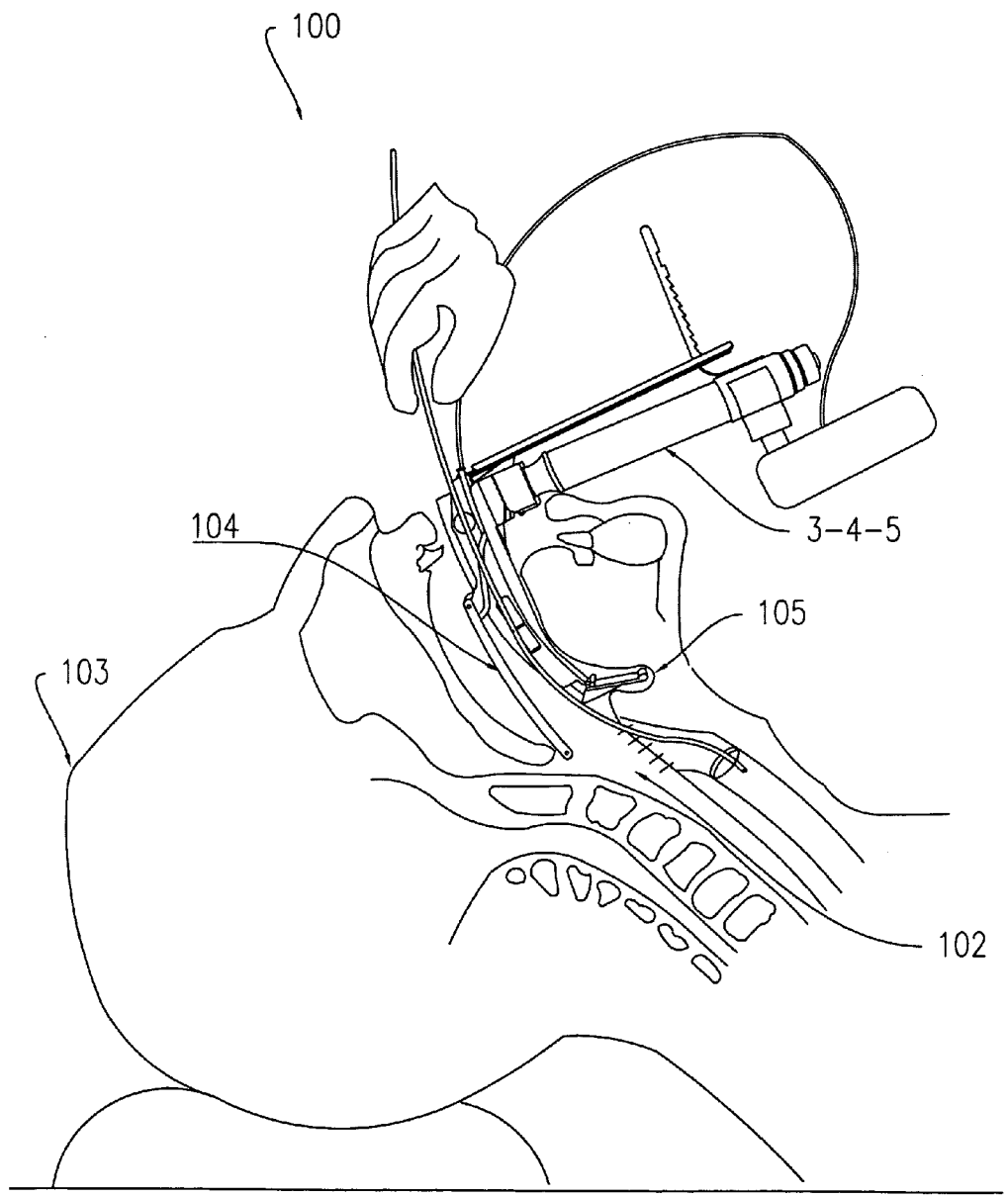
FIG. 2 is a diagrammatic side elevational view of the double-bladed laryngoscope of the embodiments of the present invention recording and locally displaying an area of interest of a patient via a readily interchangeable and sterilizable visual image recorder.

Referring now to FIG. 2, which is a diagrammatic side elevational view of the double-bladed laryngoscope of the embodiments of the present invention recording and locally displaying an area of interest of a patient via a readily interchangeable and sterilizable visual image recorder, the double-bladed laryngoscope of the embodiments of the present invention is shown generally at 100 for recording and locally displaying an area of interest 102 of a patient 103 via a readily interchangeable and sterilizable visual image recorder 104.

B. Overall Configuration of the Double-Bladed Laryngoscope 100.

Figure 3:
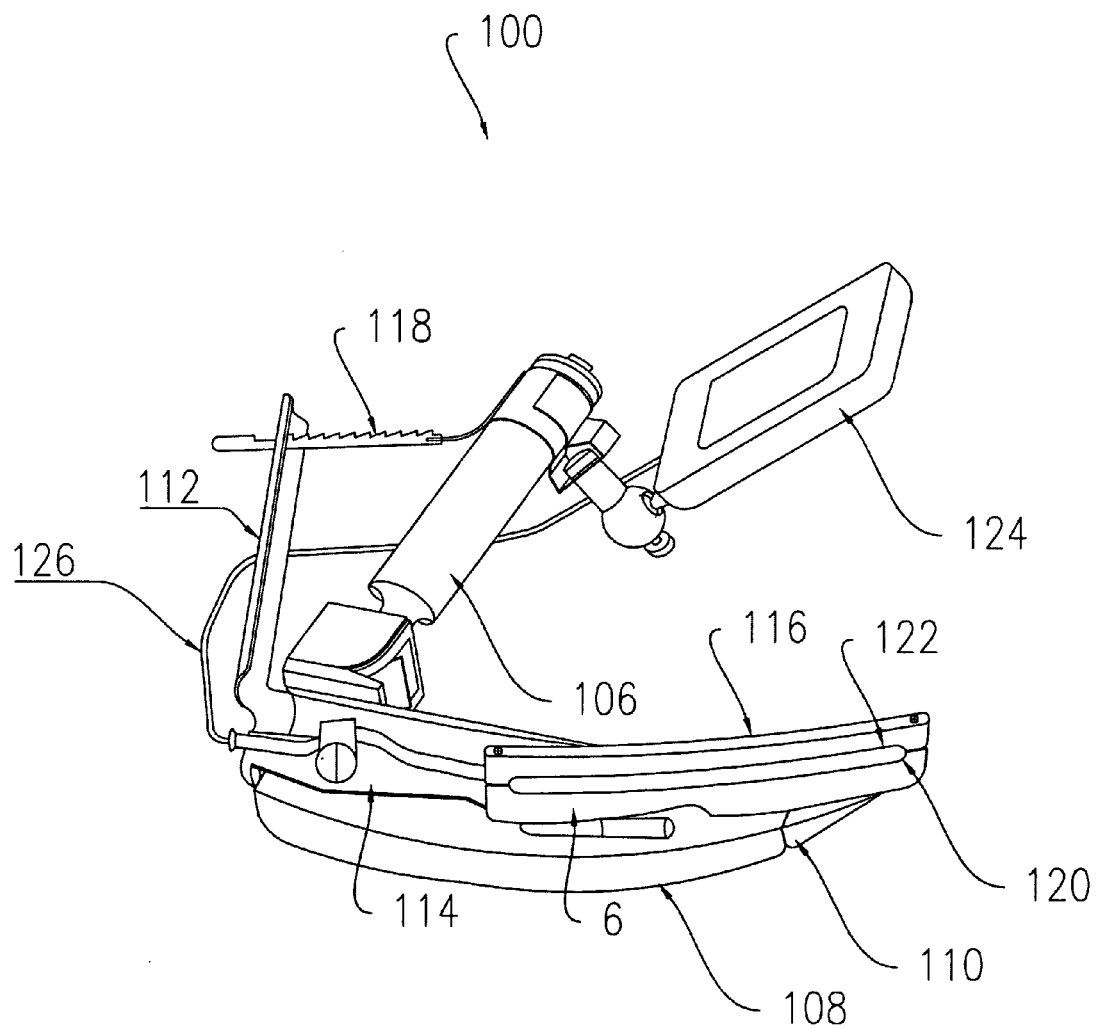
FIG. 3 is a diagrammatic perspective view of the double-bladed laryngoscope of the embodiments of the present invention identified by ARROW 3 in FIG. 2, with the blade closed.
Figure 4:
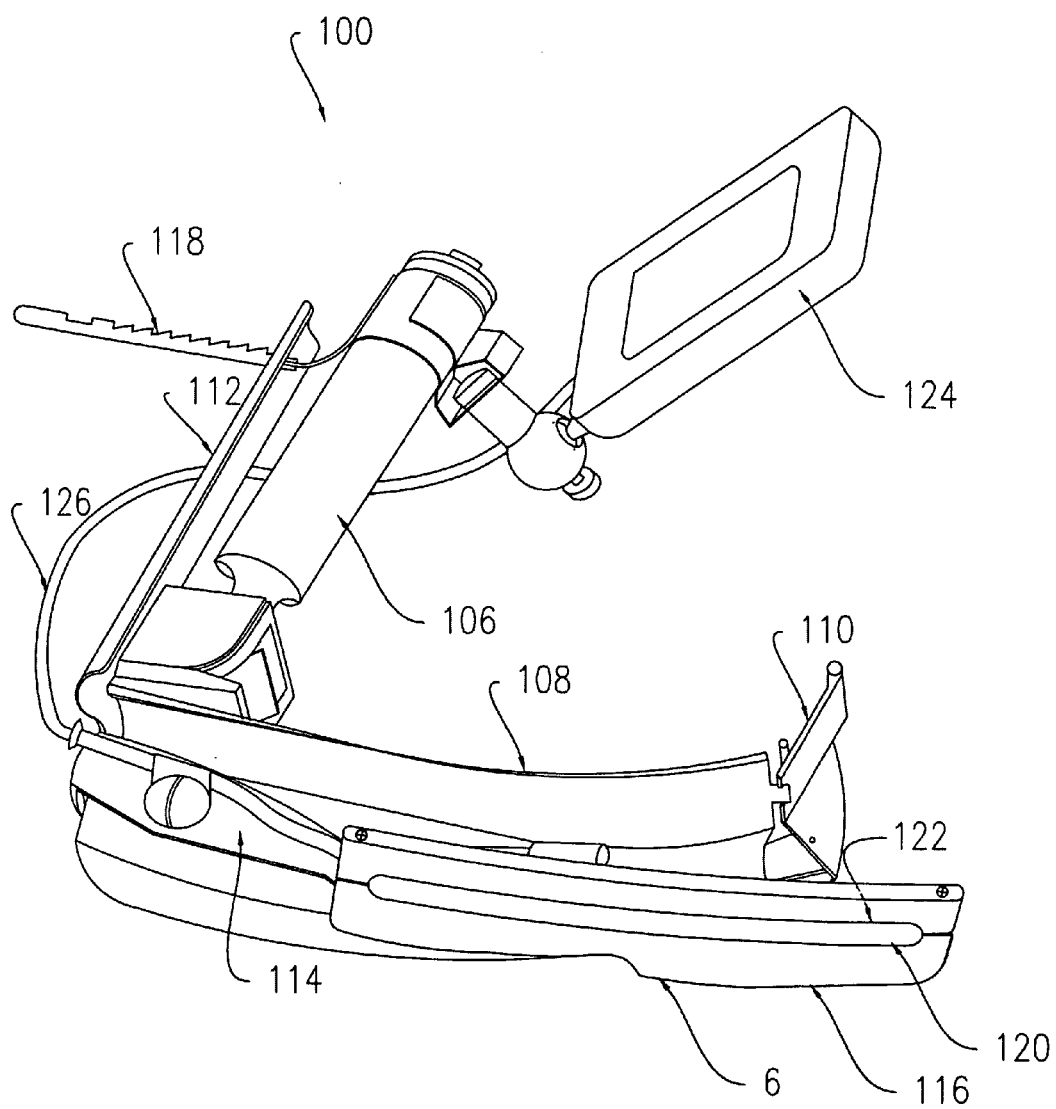
FIG. 4 is a diagrammatic perspective view of the double-bladed laryngoscope of the embodiments of the present invention identified by ARROW 4 in FIG. 2, with the blade open.
Figure 5:
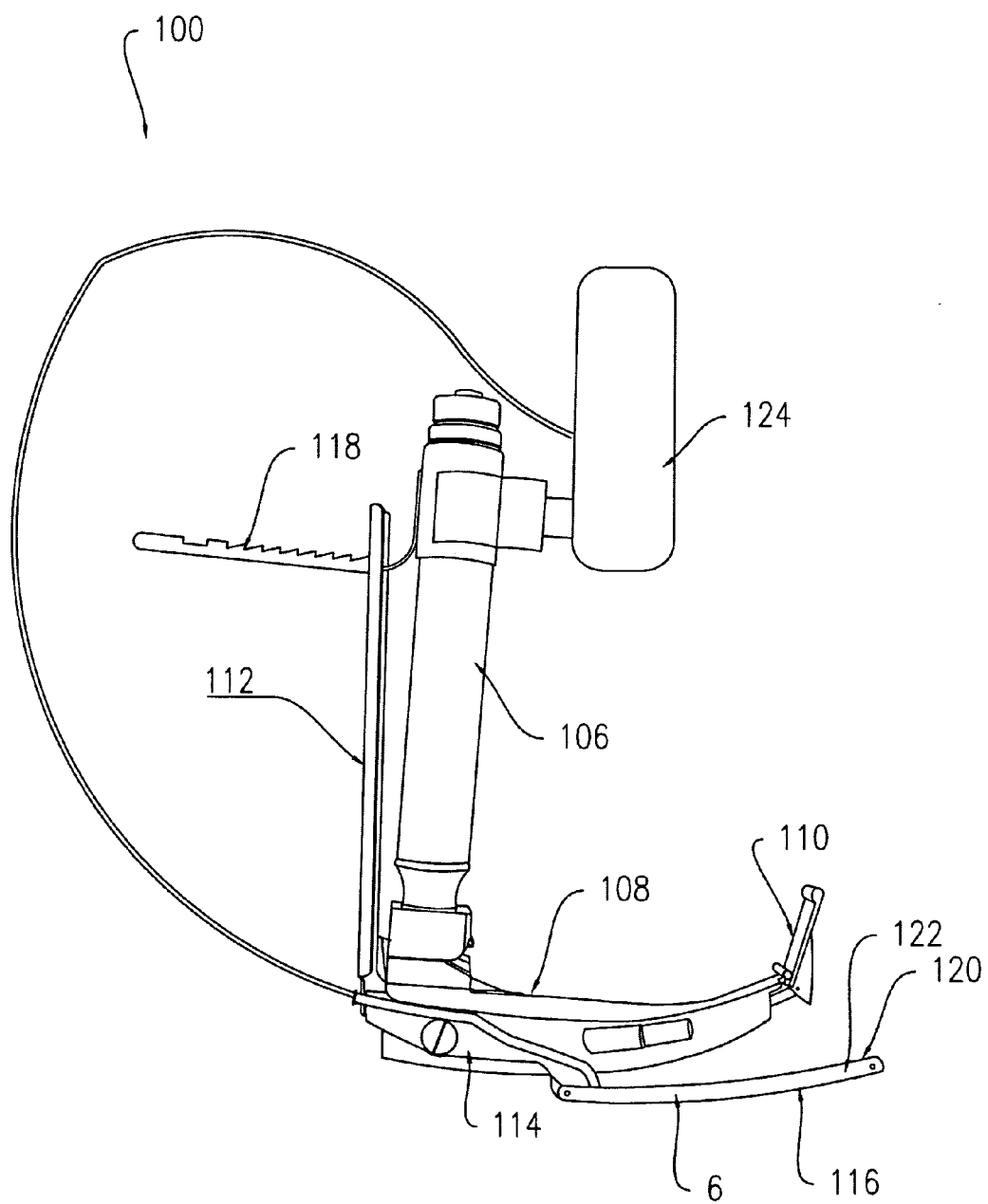
FIG. 5 is a diagrammatic side elevational view of the double-bladed laryngoscope of the embodiments of the present invention identified by ARROW 5 in FIG. 2, with the blade open.

The overall configuration of the double-bladed laryngoscope 100 can best be seen in FIGS. 3-5, which are, respectively, a diagrammatic perspective view of the double-bladed laryngoscope of the embodiments of the present invention identified by ARROW 3 in FIG. 2, with the blade closed, a diagrammatic perspective view of the double-bladed laryngoscope of the embodiments of the present invention identified by ARROW 4 in FIG. 2, with the blade open, and a diagrammatic side elevational view of the double-bladed laryngoscope of the embodiments of the present invention identified by ARROW 5 in FIG. 2, with the blade open, and as such, will be discussed with reference thereto.

The double-bladed laryngoscope 100 comprises a stationary handle 106, a stationary blade 108, a movable tip 110, a movable handle 112, a movable blade arm 114, a movable blade 116, a lock 118, and a camera arrangement 120. The stationary blade 108 is affixed to the stationary handle 106. The movable tip 110 is pivotally attached to the stationary blade 108. The movable handle 112 is pivotally attached to the stationary blade 108. When the movable handle 112 is moved toward the stationary handle 106 will bend the movable tip 110 at the valleculla 105 and will lift the epiglottis to uncover the laryngeal opening (glottis). Simultaneously the movable blade 116 pivotally attached to the stationary blade 108 and affixed to movable handle 112 by movable blade arm 114, so as to allow movable blade 116 to pivot away from stationary blade 108 spreading the posterior pharyngeal tissues and allowing space for intubating tube.

The lock 118 locks the movable blade 116 in a desired positioned by locking the movable handle 112 affixed thereto.

The camera arrangement 120 is for recording and locally displaying the area of interest 102 of the patient 103 and runs readily replaceably and interchangeably through the movable blade 116 so as to be readily removable therefrom for sterilization without compromising the structural integrity of the movable blade 116

The camera arrangement 120 comprises a camera 122, a display 124, and a conduit 126. The camera 122 of the camera arrangement 120 is disposed in movable blade 116 faces the stationary blade 108, and is readily replaceable and interchangeable so as to be readily removable from the movable blade 116 for sterilization without compromising the structural integrity of the movable blade 116. The display 124 of the camera arrangement 120 is operatively connected to the stationary handle 106. The conduit 126 of the camera arrangement 120 operatively connects the camera 122 of the camera arrangement 120 to the display 124 of the camera arrangement 120 for allowing viewing at the display 124 of the camera arrangement 120 of the area of interest 102 of the patient 103 recorded by the camera 122 of the camera arrangement 120.

C. Specific Configuration of Movable Blade 116, the Camera 122 of the Camera Arrangement 120, and the Conduit 126 of the Camera Arrangement 120.

Figure 8:
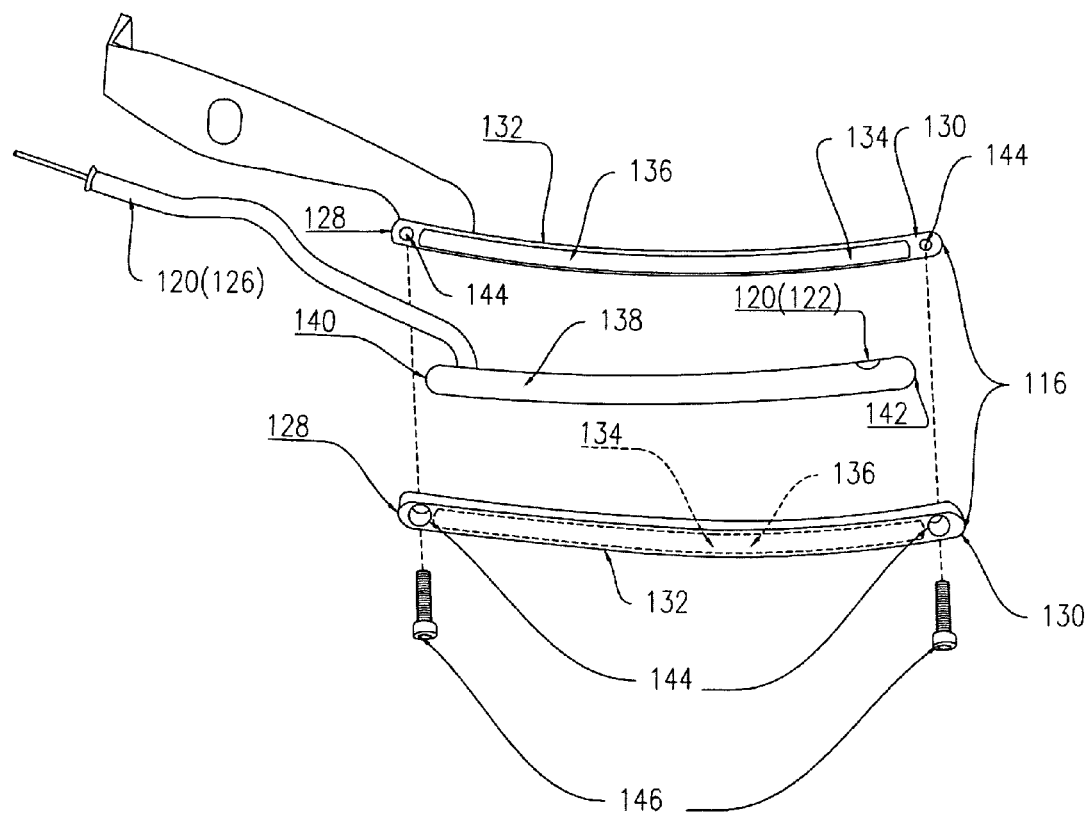
FIG. 8 is an exploded diagrammatic side elevational view of the blade identified by ARROW 6 in FIG. 6.

The specific configuration of the movable blade 116, the camera 122 of the camera arrangement 120, and the conduit 126 of the camera arrangement 120 can best be seen in FIGS. 6-8, which are, respectively, an enlarged diagrammatic perspective view of the blades identified by ARROW 6 in FIGS. 3-5, an enlarged diagrammatic cross sectional view taken along LINE 7-7 in FIG. 6, and an exploded diagrammatic side elevational view of the blade identified by ARROW 6 in FIG. 6, and as such, will be discussed with reference thereto.

(1) Movable Blade 116.

The movable blade 116 is arcuate-shaped and has a proximal end 128 and a free distal end 130.

The movable blade 116 is divided along its length, from the proximal end 128 of the movable blade 116 to the free distal end 130 of the movable blade 116, into two separate and distinct parts 132.

The two separate and distinct parts 132 of the movable blade 116 have facing surfaces 134. The facing surfaces 134 of the two separate and distinct parts 132 of the movable blade 116 have complementary channel portions 136 therein. The complementary channel portions 136 in the facing surfaces 134 of the two separate and distinct parts 132 of the movable blade 116 are arcuate-shaped like that of the movable blade 116, and extend from inward of the proximal end 128 of the movable blade 116 to inward of the free distal end 130 of the movable blade 116.

(2) Camera 122 of the Camera Arrangement 120.

The camera 122 of the camera arrangement 120 is contained within a shell 138. The shell 138 of the camera arrangement 120 is rigid, arcuate-shaped to fit complementary into the complementary channel portions 136 in the facing surfaces 134 of the two separate and distinct parts 132 of the movable blade 116 so as to be interchangeably and replaceably sandwiched between the two separate and distinct parts 132 of the movable blade 116

The shell 138 of the camera arrangement 120 has a proximal end 140 and a distal end 142. The camera 122 of the camera arrangement 120 is disposed in the shell 138 of the camera arrangement 120, inward of the distal end 142 of the shell 138 of the camera arrangement 120, and faces towards the stationary blade 108 for recording the area of interest 102 of the patient 103.

Each separate and distinct part 132 of the movable blade 116 has a pair of through bores 144. The pair of through bores 144 through each separate and distinct part 132 of the movable blade 116 are disposed between the free distal end 130 of the movable blade 116 and the complementary channel portion 136 in the facing surfaces 134 of an associated separate and distinct part 132 of the movable blade 116 and between the complementary channel portion 136 in the facing surfaces 134 of an associated separate and distinct part 132 of the movable blade 116 and the proximal end 128 of the movable blade 116

The shell 138 of the camera arrangement 120 is maintained snugly, interchangeably, and replaceably in the complementary channel portions 136 in the facing surfaces 134 of the two separate and distinct parts 132 of the stationary blade 108 by a pair of screws 146 passing through the pair of through bores 144 through each separate and distinct part 132 of the movable blade 116, respectively.

(3) Conduit 126 of the Camera Arrangement 120.

The conduit 126 of the camera arrangement 120 extends rearwardly and upwardly from the shell 138 of the camera arrangement 120, inward of the distal end 140 of the shell 138 of the camera arrangement 120 so as not to interfere with the movable blade 116.

D. Impressions.

It will be understood that each of the elements described above or two or more together may also find a useful application in other types of constructions differing from the types described above.

While the embodiments of the present invention have been illustrated and described as embodied in a double-bladed laryngoscope for recording and locally displaying a field of view thereof via a readily interchangeable and sterilizable visual image recorder and a blade therefor, however, they are not limited to the details shown, since it will be understood that various omissions, modifications, substitutions, and changes in the forms and details of the embodiments of the present invention illustrated and their operation can be made by those skilled in the art without departing in any way from the spirit of the embodiments of the present invention.

Without further analysis the foregoing will so fully reveal the gist of the embodiments of the present invention that others can by applying current knowledge readily adapt them for various applications without omitting features that from the standpoint of prior art fairly constitute characteristics of the generic or specific aspects of the embodiments of the present invention.

The invention claimed is:

1. An improved double-bladed laryngoscope for recording and locally displaying an area of interest of a patient via a readily interchangeable and sterilizable visual image recorder and being of the type having a stationary handle, a stationary blade affixed to the stationary handle, a movable tip pivotally attached to a stationary blade, a movable tip arm pivotally attached to the movable tip and movable handle, when the movable handle is moved towards the stationary handle will bend the movable tip lifting the epiglottis, to uncover laryngeal opening (glottis), simultaneously a movable blade pivotally attached to stationary blade and affixed to movable handle by movable blade arm so as to allow movable blade to pivot away from stationary blade spreading posterior pharyngeal tissues and allowing space for intubating tube, a lock locks the movable blade in a desired positioned by locking the movable handle affixed thereto, and a camera arrangement for recording and locally displaying the area of interest of the patient, wherein said improvement comprises:

a) the camera arrangement running readily replaceably and interchangeably through the movable blade so as to be readily removable therefrom for sterilization without compromising the structural integrity of the movable blade;

b) the camera arrangement comprising:
  I) a camera;
  ii) a display; and
  iii) a conduit;

c) the movable blade having a proximal end and a free distal end; and d) the movable blade being divided along its length, from the proximal end of the movable blade to the free distal end of the movable blade, into two separate and distinct parts.

2. The laryngoscope of claim 1, wherein said improvement comprises:
   a) the camera of the camera arrangement being disposed in the movable blade;
   b) the camera of the camera arrangement facing the stationary blade; and
   c) the camera of the camera arrangement being readily replaceable and interchangeable so as to be readily removable from the movable blade for sterilization without compromising the structural integrity of the movable blade.

3. The laryngoscope of claim 1, wherein said improvement comprises the display of the camera arrangement being operatively connected to the stationary handle.

4. The laryngoscope of claim 1, wherein said improvement comprises the conduit of the camera arrangement operatively connecting the camera of the camera arrangement to the display of the camera arrangement for allowing viewing at the display of the camera arrangement of the area of interest of the patient recorded by the camera of the camera arrangement.

5. The laryngoscope of claim 1, wherein said improvement comprises the movable blade being arcuate-shaped.

6. The laryngoscope of claim 1, wherein said improvement comprises:
   a) the two separate and distinct parts of the movable blade having facing surfaces;
   b) the facing surfaces of the two separate and distinct parts of the movable blade having complementary channel portions, respectively;
   c) the complementary channel portions in the facing surfaces of the two separate and distinct parts of the movable blade, respectively, being arcuate-shaped like that of the movable blade; and
   d) the complementary channel portions in the facing surfaces of the two separate and distinct parts of the movable blade, respectively, extending from inward of the proximal end of the movable blade to inward of the free distal end of the movable blade.

7. The laryngoscope of claim 6, wherein said improvement comprises the camera of the camera arrangement being contained within a shell.

8. The laryngoscope of claim 7, wherein said improvement comprises the shell of the camera arrangement being:
   a) rigid; and
   b) arcuate-shaped to fit complementary into the complementary channel portions in the facing surfaces of the two separate and distinct parts of the movable blade, respectively, so as to be interchangeably and replaceably sandwiched between the two separate and distinct parts of the movable blade.

9. The laryngoscope of claim 7, wherein said improvement comprises:
   a) the shell of the camera arrangement having a proximal end and a distal end;
   b) the camera of the camera arrangement being disposed in the shell of the camera arrangement;
   c) the camera of the camera arrangement being disposed inward of the distal end of the shell of the camera arrangement; and
   d) the camera of the camera arrangement facing towards the stationary blade for recording the area of interest of the patient.

10. The laryngoscope of claim 9, wherein said improvement comprises:
    a) the conduit of the camera arrangement extending rearwardly and upwardly from the shell of the camera arrangement; and
    b) the conduit of the camera arrangement extending from inward of the proximal end of the shell of the camera arrangement so as not to interfere with the movable blade.

11. The laryngoscope of claim 7, wherein said improvement comprises:
    a) each separate and distinct part of the movable blade having a pair of through bores; and
    b) the pair of through bores through each separate and distinct part of the movable blade being disposed between the free distal end of the movable blade and the complementary channel portion in the facing surfaces of an associated separate and distinct part of the movable blade and between the complementary channel portion in the facing surfaces of an associated separate and distinct part of the stationary blade and the proximal end of the movable blade.

12. The laryngoscope of claim 11, wherein said improvement comprises the shell of the camera arrangement being maintained snugly, interchangeably, and replaceably in the complementary channel portions in the facing surfaces of the two separate and distinct parts of the movable blade by a pair of screws passing through the pair of through bores through each separate and distinct part of the movable blade, respectively.

13. A laryngoscope blade for recording an area of interest of a patient via a visual image recorder that is readily interchangeable and sterilizable, comprising:
    a) a movable blade; and
    b) a camera arrangement;
    wherein said camera arrangement is for recording the area of interest of the patient;
    wherein said camera arrangement is readily interchangeably and replaceably connected to said movable blade so as to be readily interchangeable and sterilizable;
    wherein said camera arrangement comprises:
        I) a camera;
        ii) a display; and
        iii) a conduit;
    wherein said movable blade had a proximal end and a free distal end; and
    wherein said movable blade is divided along its length, from said proximal end of said movable blade to said free distal end of said movable blade, into two separate and distinct parts.

14. The laryngoscope blade of claim 13, wherein said camera of said camera arrangement is disposed in said movable blade;
    wherein said camera of said camera arrangement faces said stationary blade; and
    wherein said camera of said camera arrangement is readily replaceable and interchangeable so as to be readily removable from said movable blade for sterilization without compromising the structural integrity of said movable blade.

15. The laryngoscope of claim 13, wherein said display of said camera arrangement is operatively connected to said stationary handle.

16. The laryngoscope of claim 13, wherein said conduit of said camera arrangement operatively connects said camera of said camera arrangement to said display of said camera arrangement for allowing viewing at said display of said camera arrangement of the area of interest of the patient recorded by said camera of said camera arrangement.

17. The laryngoscope of claim 13, wherein said movable blade is arcuate-shaped.

18. The laryngoscope of claim 13, wherein said two separate and distinct parts of said movable blade have facing surfaces, respectively;
   wherein said facing surfaces of said two separate and distinct parts of said movable blade have complementary channel portions, respectively;
   wherein said complementary channel portions in said facing surfaces of said two separate and distinct parts of said movable blade, respectively, are arcuate-shaped like that of said movable blade; and
   wherein said complementary channel portions in said facing surfaces of said two separate and distinct parts of said movable blade, respectively, extend from inward of said proximal end of said movable blade to inward of said free distal end of said movable blade.

19. The laryngoscope of claim 13, wherein said camera of said camera arrangement is contained within a shell.

20. The laryngoscope of claim 19, wherein said shell of said camera arrangement is rigid; and
   wherein said shell of said camera arrangement is arcuate-shaped to fit complementary into said complementary channel portions in said facing surfaces of said two separate and distinct parts of said movable blade, respectively, so as to be interchangeably and replaceably sandwiched between said two separate and distinct parts of said movable blade.

21. The laryngoscope of claim 19, wherein said shell of said camera arrangement has a proximal end and a distal end;
   wherein said camera of said camera arrangement is disposed in said shell of said camera arrangement;
   wherein said camera of said camera arrangement is disposed inward of said distal end of said shell of said camera arrangement; and
   wherein said camera of said camera arrangement faces towards said stationary blade for recording the area of interest of the patient.

22. The laryngoscope of claim 21, wherein said conduit of said camera arrangement extends rearwardly and upwardly from said shell of said camera arrangement; and
   wherein said conduit of said camera arrangement extends from inward of said proximal end of said shell of said camera arrangement so as not to interfere with said movable blade.

23. The laryngoscope of claim 19, wherein each separate and distinct part of said movable blade has a pair of through bores; and
   wherein said pair of through bores through each separate and distinct part of said movable blade are disposed between said free distal end of said movable blade and said complementary channel portion in said facing surfaces of an associated separate and distinct part of said movable blade and between said complementary channel portion in said facing surfaces of said associated separate and distinct part of said movable blade and said proximal end of said movable blade.

24. The laryngoscope of claim 23, wherein said shell of said camera arrangement is maintained snugly, interchangeably, and replaceably in said complementary channel portions in said facing surfaces of said two separate and distinct parts of said movable blade, respectively, by a pair of screws passing through said pair of through bores through each separate and distinct part of said movable blade, respectively.

* * * * *